United States Patent [19]

Temple, Jr. et al.

[11] 4,386,091
[45] May 31, 1983

[54] 2-PHENOXYALKYL-1,2,4-TRIAZOL-3-ONE ANTIDEPRESSANTS

[75] Inventors: Davis L. Temple, Jr.; Walter G. Lobeck, Jr., both of Evansville, Ind.

[73] Assignee: Mead Johnson & Company, Evansville, Ind.

[21] Appl. No.: 351,833

[22] Filed: Feb. 24, 1982

[51] Int. Cl.³ .............. A61K 31/495; C07D 249/08; C07D 295/00
[52] U.S. Cl. .................. 424/250; 544/366; 548/263; 548/265
[58] Field of Search .............. 544/366; 424/250; 548/263, 265

[56] References Cited
U.S. PATENT DOCUMENTS

| 3,381,009 | 4/1968 | Palazzo et al. | 544/366 |
| 3,857,845 | 12/1974 | Palazzo | 544/366 |
| 4,338,317 | 7/1982 | Temple, Jr. et al. | 544/366 |

Primary Examiner—Donald G. Daus
Assistant Examiner—Sharon A. Gibson
Attorney, Agent, or Firm—Robert H. Uloth; Richard P. Ryan

[57] ABSTRACT

Phenoxyalkyl substituted-1,2,4-triazolones having antidepressant properties typified by 4-[3-[4-(3-chlorophenyl)-1-piperazinyl]propyl]-5-ethyl-2,4-dihydro-2-(2-phenoxyethyl)-3H-1,2,4-triazol-3-one are disclosed.

7 Claims, No Drawings

2-PHENOXYALKYL-1,2,4-TRIAZOL-3-ONE ANTIDEPRESSANTS

BACKGROUND OF THE INVENTION

The present invention relates to 1,2,4-triazole heterocyclic carbon compounds and to their preparation and use. More particularly, the invention relates to 4-[3-[4-(halo-phenyl)-1-piperazinyl]propyl]-5-ethyl-2,4-dihydro-2-(phenoxyalkyl)-3H-1,2,4-triazol-3-ones and therapeutic use in treating depression.

U.S. Pat. No. 3,857,845 to G. Palazzo describes the compound 1-[3-(4-meta-chlorophenyl-1-piperazinyl)-propyl]-3,4-diethyl-$\Delta^2$-1,2,4-triazolin-5-one depicted structurally below.

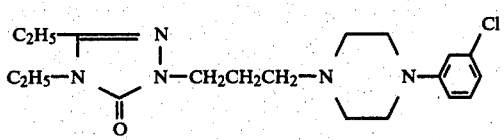

Alternatively, the compound can be named 2-[3-[4-(3-chlorphenyl)-1-piperazinyl]propyl]-4,5-diethyl-2H-1,2,4-triazol-3(4H)-one, and is commonly called etoperidone.

Regarding utility, the '845 Palazzo patent discloses that etoperidone has pharmacological properties typical of tranquilizers including sedation, reduced activity towards the experimentor and lower motor activity. In addition, hypotensive and analgesic activity are reported with possible use as an antianxiety agent and tranquilizer in human therapy mentioned.

U.S. Pat. No. 3,381,009 to G. Palazzo, et al., discloses 1,2,4-triazolo[4,3-a]pyridines of the following general formula

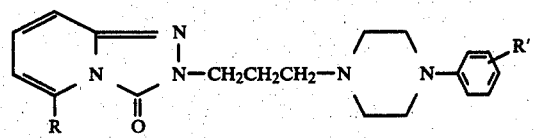

wherein R is hydrogen or methyl and R' is hydrogen, alkyl (1-4C), alkoxy (1-4C), or halogen. The compounds are said to exhibit tranquilizing action, hypotensive action, and analgesic action according to various animal tests. With respect to tranquilizing action, the pharmacological profile includes such behavioral effects as sedation, decrease in motor activity, hypotonia, high dose induced muscular non-coordination and ataxia, and inhibition of conditioned reflexes in the rat. According to the '009 patent, data relative to behavioral, adrenolytic and anti-serotonin effects indicate that the compounds resemble major tranquilizers, such as chlorpromazine more than minor ones such as meprobamate. Pharmacological properties of one compound in particular, 2-[3-[4-(3-chlorophenyl)-1-piperazinyl]propyl]-1,2,4-triazolo[4,3-a]pyridin-3(2H)-one, have been described in more detail by Silvestrini, et al., International Journal of Neuropharmacology, 7, 587–599 (1968). The aforementioned compound, commonly known as trazodone, has been studied extensively in man and is considered to be an antidepressive equivalent in effectiveness to imipramine but with fewer side effects (Fabre, et al., Current Therapeutic Research, 25, 827–834 (1979)).

SUMMARY OF THE INVENTION AND DESCRIPTION OF PREFERRED EMBODIMENTS

Broadly described, the present invention is concerned with piperazinylalkyl-1,2,4-triazol-3-ones characterized by Formula I

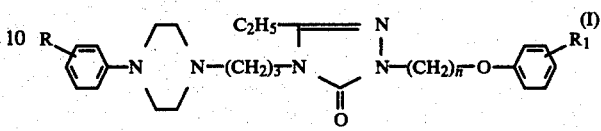

wherein n is the integer 2-4, R is halogen, $R_1$ is hydrogen, halogen or alkoxy, and pharmaceutically acceptable salts thereof. The term "halogen" or halo as used herein comprehends fluorine, iodine and most preferably bromine and chlorine. The term alkoxy as used herein comprehends from 1 to 4 carbon atoms, such as methoxy, ethoxy, tert-butoxy and the like.

The pharmaceutically acceptable acid addition salts are those in which the anion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation purposes such as solubility, lack of hygroscopicity, compressibility with respect to tablet formation and compatibility with other ingredients with which the substance may be used for pharmaceutical purposes. The salts are made by reaction of the base of Formula I with the selected acid preferably by contact in solution. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include hydrochloric, hydrobromic, hydroiodic, citric, acetic, benzoic, mandelic, phosphoric, nitric, mucic, isethionic, palmitic, heptanoic, and others.

The Formula I compounds are useful pharmacological agents with psychotropic properties. In this regard, they exhibit selective central nervous system effects associated with antidepressant activity according to conventional in vivo test systems such as those listed below.

| Behavioral Test | Reference |
|---|---|
| Suppression of conditioned avoidance response (CAR) | Albert, et al., Pharmacologist, 4, 152 (1962). |
| Prevention of reserpine ptosis in mice (antidepressant) | Niemegeers, Industrial Pharmacology, Vol. 2 - Antidepressants, Ed. by S. Fielding and H. Lal, pp. 73–98, Futura, New York, N.Y., (1975). |
| Potentiation of alcohol Hypnois in the mouse (sedative) | — |

As further indication of the psychotropic activity and specificity of the instant compounds, state of the art in vitro central nervous system receptor binding methodology can be employed. Certain compounds (commonly referred to as ligands) have been identified which preferentially bind to specific high affinity sites in brain tissue dealing with psychotropic activity or potential for side effects. Inhibition of radiolabeled ligand binding to such specific high affinity sites is considered a measure of a compound's ability to affect corresponding central nervous system function or cause side effects in vivo.

The following tests, as well as others, can be employed in developing a profile of the psychotropic activity of the instant compounds.

| Receptor Binding Assay | Reference |
| --- | --- |
| Dopamine | Burt, et al., Molec. Pharmacol., 12, 800 (1976); Science, 196, 326 (1977); Creese, et al, Science, 192, 481 (1976). |
| Cholinergic | Yamamura, et al., Proc. Natn. Acad. Sci. USA 71 1725 (1974). |
| Alpha-receptor | Crews, at al., Science 202: 322 (1978). Rosenblatt, et al., Brain Res. 160: 186 (1979) U'Prichard, et al., Science 199: 197 (1978). U'Prichard, et al., Molec. Pharmacol. 13: 454 (1977). |
| Serotonin Type 2 | Peroutka and Snyder, Molec. Pharmacol. 16: 687 (1979). |

According to the foregoing assays, 4-[3-[4-(3-chlorophenyl-1-piperazinyl]propyl]-5-ethyl-2,4-dihydro-2-(2-phenoxyethyl)-3$\underline{H}$-1,2,4-triazol-3-one (a representative compound of Formula I) inhibits serotonin binding and was relatively inactive with respect to dopamine receptor binding, cholinergic receptor binding, and alpha-receptor binding. The latter is particularly significant in that drugs with high affinity for alpha-receptors relative to serotonin type 2 receptors are likely to cause side effects such as sedation and blood pressure lowering. Thus, the instant compounds are considered improved antidepressants with minimal side effect potential.

According to the present invention, the piperazinylalkyl-1,2,4-triazol-3-ones characterized by Formula I are obtained by the following process which comprises reacting a piperazinylalkyltriazolone of Formula II

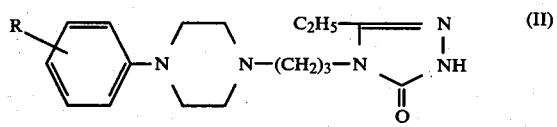

wherein R is halogen attached in the 2, 3 or 4 position of the phenyl ring with a phenoxyalkylhalide of Formula III

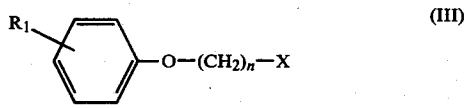

wherein $R_1$ is as defined above, n is the integer 2–4 and "X" comprehends halogen, preferably chlorine or bromine, or a suitable leaving group such as sulfate, phosphate, tosylate, mesylate, and the like, in the presence of a suitable alkali metal base such as sodium hydroxide, potassium hydroxide, sodium carbonate or potassium carbonate in a reaction inert solvent such as xylene or acetonitrile and the like.

Standard laboratory procedures are employed in carrying out the foregoing reaction such as those described for the alkylation step of the Gabriel synthesis- S. Gabriel, Ber. 20, 2224 (1887). In the present case, the reactants are combined in an inert reaction solvent at temperatures ranging from about 50° C. to 200° C. Acetonitrile and xylene are particularly preferred solvents for carrying out the reaction but other solvents which do not adversely affect the reaction or reactants can be employed. In this regard, solvents such as benzene, toluene dimethylformamide, n-butanol, and the like are suitable. The reaction period varies to some extent depending on solvent and temperature selected. For instance, at lower temperatures, long reaction periods are needed while at higher temperatures, alkylation is completed in a shorter time. In the case of acetonitrile or xylene, optimum yields are obtained with a reaction period of 8 to 68 hours.

A particularly preferred embodiment of the above process for preparing Formula I products comprises reacting a piperazinylalkyltriazolone of Formula II with a phenoxyalkylhalide of Formula III in the presence of an alkali metal carbonate such as potassium carbonate or sodium carbonate in acetonitrile.

The Formula II piperazinylalkyltriazolone intermediates are prepared by heating N-ethoxycarbonylthiopropionamide with hydrazine in ethanol to provide the triazolone compound of Formula IV

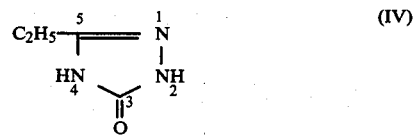

which is then alkylated with a 1-(halophenyl)-4-(3-halopropyl)piperazine of Formula V

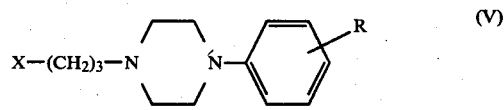

wherein R is halogen and X comprehends halogen, preferably chlorine or bromine, or a suitable leaving group such as sulfate, phosphate, tosylate, mesylate, and the like, in the presence of a suitable alkali metal base such as sodium carbonate, potassium carbonate, potassium hydroxide, sodium hydroxide and the like in a reaction inert solvent. Laboratory procedures and solvents (preferably acetonitrile) previously disclosed as operable for the alkylation of Formula II intermediates with Formula VII phenoxyalkyl halides are employed.

Another aspect of the instant invention provides a method for treating a mammal afflicted with depression which comprises administering systemically to said mammal a therapeutically effective antidepressant amount of a compound of Formula I or a pharmaceutically acceptable acid addition salt thereof. An effective dose ranges from 0.01 to 40 mg/kg of body weight with the dosage dependent on effects sought, manner of administration, and to some extent with the particular compound selected. Systemic administration refers to oral, rectal and parenteral (i.e. intramuscular, intravenous and subcutaneous). Generally, it will be found that when a compound of the present invention is administered orally, a larger quantity of the active agent is required to produce the same effect as a smaller quantity given parenterally. In accordance with good clinical practice, it is preferred to administer the instant compounds at a concentration level that will produce effective antidepressant effects without causing any harmful or untoward side effects.

The compounds of the present invention may be administered for antidepressant purposes either as individual therapeutic agents or as mixtures with other therapeutic agents. Therapeutically, they are generally given as pharmaceutical compositions comprised of an antidepressant amount of a compound of Formula I or a pharmaceutically acceptable salt thereof and a pharmaceutically acceptable carrier. Pharmaceutical compositions which provide from about 1 to 500 mg. of the active ingredient per unit dose are preferred and are conventionally prepared as tablets, lozenges, capsules, powders, aqueous or oily suspensions, syrups, elixirs and aqueous solutions.

The nature of the pharmaceutical composition employed will, of course, depend on the desired route of administration. For example, oral compositions may be in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection.

The following non-limiting examples illustrate the process and products of this invention. Nuclear magnetic resonance (NMR) spectral characteristics refer to chemical shifts down field ($\delta$) expressed as parts per million (ppm) versus tetramethylsilane as reference standard. The relative area reported for the various shifts corresponds to the number of hydrogen atoms in the individual substituent and the nature of the shifts as to multiplicity is reported as broad singlet (bs), multiplet (m), triplet (t), or quadruplet (q) with coupling constant reported where appropriate. The format is NMR (solvent): $\delta$(relative area, multiplicity, J value). Abbreviations employed are DMSO-$d_6$ (deuterodimethylsulfoxide), IR (infrared), and KBr (potassium bromide).

EXAMPLE 1

4-[3-[4-(3-Chlorophenyl)-1-piperazinyl]propyl]-5-ethyl-2,4-dihydro-3H-1,2,4-triazol-3-one (IIa)

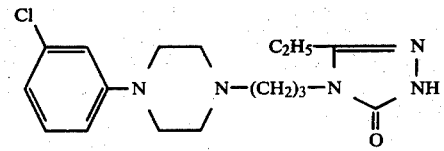

(a) 1-(3-Chloropropyl)-4-(3-chlorphenyl)piperazine Hydrochloride

A 50% sodium hydroxide solution (430.6 g., 5.333 mole) is added dropwise to a stirred solution of 1-(3-chlorophenyl)piperazine hydrochloride (502.0 g., 2.153 mole) and 1-bromo-3-chloropropane (339.0 g., 2.153 mole) in 435 ml. water and 535 ml. acetone while maintaining temperature of 0°–10° C. Stirring is continued for a 16 hr. period at room temperature and the upper organic phase then separated and concentrated under reduced pressure. The remaining residual oil is taken up in 500 ml. acetone, filtered and the filtrate concentrated under reduced pressure to an oily residue which is dissolved in boiling dilute hydrochloric acid (1.67 liter water plus 280 ml. concentrated HCl, 3.36 mole). The oil which initially separates from the cooled acid solution, solidifies on standing and is collected, rinsed with cold water and air dried. Crystallization of this material from water employing activated charcoal affords 438.4 g. (66%) of 1-(3-chloropropyl)-4-(3-chlorophenyl)piperazine hydrochloride, m.p. 196.5°–198.5° C. The hydrochloride salt is converted to the free base with aqueous 10% sodium hydroxide and recovered by extracting with ether (dried over magnesium sulfate). Concentration of the etheral extract affords 1-(3-chloropropyl)-4-(3-chlorophenyl)piperazine free base as an oily residue.

(b) Reaction in Xylene

Sodium hydroxide (4.2 g., 0.105 mole) in 20 ml. of water is added to 5-ethyl-2,4-dihydro-3H-1,2,4-triazol-3-one (11.96 g., 0.105 mole) obtained according to the procedure of *J. Org. Chem.*, 41, 3233–3237 (1976) in 120 ml. of ethanol. Following addition, distillables are removed under reduced pressure, ethanol added to residual material and removed under reduced pressure and the process repeated until the sodium salt of 5-ethyl-2,4-dihydro-3H-1,2,4-triazol-3-one is obtained as a dry solid.

The sodium salt is pulverized, suspended in 600 ml. of xylene and mixed with 1-(3-chloropropyl)-4-(3-chlorophenyl)piperazine free base (28.6 g., 0.105 mole). The resulting mixture is refluxed with stirring for 60 hrs. and the reaction mixture filtered and concentrated under reduced pressure. Residual material taken up in 40 ml. of ethanol and acidified with ethanolic hydrogen chloride provides, on standing, 8.7 g. of solid further purified by crystallization from ethanol to afford 6.3 g. (15.5% yield) of 4-[3-[4-(3-chlorophenyl)-1-piperazinyl]propyl]-5-ethyl-2,4-dihydro-3H-1,2,4-triazol-3-one hydrochloride, m.p. 213°–215° C.

An analytical sample prepared in a similar manner melted at 210°–212° C.

Anal. Calcd. for $C_{17}H_{24}ClN_5O \cdot HCl$: C, 52.85; H, 6.52; N, 18.13. Found: C, 53.03; H, 6.47; N, 18.16.

NMR (DMSO-$d_6$): 1.17 (3H, t, 7.3 Hz); 2.09 (2H, m); 2.57 (2H, q, 7.3 Hz); 3.19 (8H, m); 3.62 (4H, m); 6.92 (3H, m); 7.23 (1H, t, 7.7 Hz); 11.40 (1H, bs).

$^{13}$C NMR (ppm): 9.56, 18.36, 23,36, 37.43, 45.07, 50.51, 52.92, 113.98, 115.07, 118.91, 130.48, 133.87, 148.07, 150.90, 155.15.

(c) Reaction in Acetonitrile With Potassium Carbonate

A mixture of 5-ethyl-2,4-dihydro-3H-1,2,4-triazol-3-one (11.3 g., 0.1 mole), 1-(3-chloropropyl)-4-(3-chlorophenyl)piperazine (27.32 g., 0.1 mole), pulverized potassium carbonate (27.64 g., 0.2 mole) and a trace of potassium iodide in 230 ml. of acetonitrile is refluxed for 18 hrs. and filtered. Concentration of the filtrate under reduced pressure and acidification of residual material in ethanol with ethanolic hydrogen chloride provides the hydrochloride salt purified by crystallization from ethanol to afford 11.0 g. (28.6% yield) of 4-[3-[4-(3-chlorophenyl)-1-piperazinyl]propyl]-5-ethyl-2,4-dihydro-3H-1,2,4-triazol-3-one hydrochloride, m.p. 209°–211° C.

EXAMPLE 2

4-[3-[4-(3-Chlorophenyl)-1-piperazinyl]propyl]-5-ethyl-2,4-dihydro-2-(2-phenoxyethyl)-3H-1,2,4-triazol-3-one (Ia)

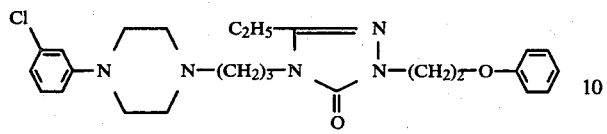

(a) Reaction in Xylene

Sodium hydroxide (1.2 g., 0.03 mole) in 5–10 ml. of water is added to 4-[3-[4-(3-chlorophenyl)-1-piperazinyl]propyl]-5-ethyl-2,4-dihydro-3H-1,2,4-triazol-3-one hydrochloride (5.8 g., 0.015 mole) in 100 ml. of ethanol. After mixing, distillables are removed under reduced pressure and residual material repeatedly taken up in ethanol and concentrated until the dry sodium salt of 4-[3-[4-(3-chlorophenyl)-1-piperazinyl]propyl]-5-ethyl-2,4-dihydro-3H-1,2,4-triazol-3-one is obtained as a hard solid.

The sodium salt is pulverized, suspended in 100 ml. of xylene and mixed with phenoxyethyl bromide (3.02 g., 0.015 mole). The resulting mixture is refluxed with stirring for a 60–70 hr. period and the hot reaction mixture filtered and concentrated under reduced pressure to provide 7.46 g., of the crude free base as an oil. Purification of the free base is carried out chromatographically employing a silica column with ethanol/chloroform eluent. Free base, obtained from the chromatographic separation, is converted to the hydrochloride salt and crystallized from ethanol to afford 2.8 g. (37% yield) of analytically pure 4-[3-[4-(3-chlorophenyl)-1-piperazinyl]propyl]-5-ethyl-2,4-dihydro-2-(2-phenoxyethyl)-3H-1,2,4-triazol-3-one hydrochloride, m.p. 182°–184° C.

Anal. Calcd. for $C_{25}H_{32}ClN_5O_2 \cdot HCl$: C, 59.29; H, 6.57; N, 13.83. Found: C, 59.37; H, 6.74; N, 13.53.

NMR (DMSO-$d_6$): 1.18 (3H, t, 7.2 Hz); 2.15 (2H, m); 2.62 (2H, q, 7.2 Hz); 3.18 (6H, m); 3.68 (6H, m); 4.01 (2H, t, 6.0 Hz); 4.25 (2H, t, 6.0 Hz); 6.95 (6H, m); 7.28 (3H, m); 11.70 (1H, bs).

(b) Reaction in Acetonitrile With Potassium Carbonate

A mixture of 4-[3-[4-(3-chlorophenyl)-1-piperazinyl]propyl]-5-ethyl-2,4-dihydro-3H-1,2,4-triazol-3-one hydrochloride (10.8 g., 0.028 mole), phenoxyethyl bromide (5.83 g., 0.028 mole), potassium carbonate (11.6 g., 0.084 mole) and a trace of potassium iodide in 100 ml. of acetonitrile is refluxed for a 66 hr. period. The hot reaction mixture is filtered, the filtrate concentrated under reduced pressure and residual material taken up in chloroform. The chloroform solution is washed with water, dried over magnesium sulfate, and concentrated under reduced pressure to provide 13.2 g. of the free base product, 4-[3-[4-(3-chlorophenyl)-1-piperazinyl]propyl]-5-ethyl-2,4-dihydro-2-(2-phenoxyethyl)-3H-1,2,4-triazol-3-one. The free base is converted to the hydrochloride salt in ethanol with ethanolic hydrogen chloride and crystallized from ethanol to afford a 71% yield of analytically pure 4-[3-[4-(3-chlorophenyl)-1-piperazinyl]propyl]-5-ethyl-2,4-dihydro-2-(2-phenoxyethyl)-3H-1,2,4-triazol-3-one hydrochloride, m.p. 175°–177° C.

Anal. Calcd. for $C_{25}H_{32}ClN_5O_2 \cdot HCl$: C, 59.29; H, 6.57; N, 13.83. Found: C, 59.04; H, 6.61; N, 13.98.

NMR (DMSO-$d_6$): 1.18 (3H, t, 7.2 Hz); 2.16 (2H, m); 2.62 (2H, q, 7.2 Hz); 3.18 (6H, m); 3.68 (6H, m); 4.01 (2H, t, 6.0 Hz); 4.25 (2H, t, 6.0 Hz); 6.95 (6H, m); 7.28 (3H, m); 11.70 (1H, bs).

EXAMPLE 3

4-[3-[4-(3-Chlorophenyl)-1-piperazinyl]propyl]-5-ethyl-2,4-dihydro-2-(3-phenoxypropyl)-3H-1,2,4-triazol-3-one (Ib)

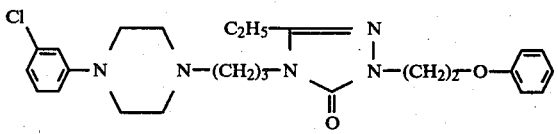

A mixture of 3-phenoxypropyl bromide (3.01 g., 0.014 mole), 4-[3-[4-(3-chlorophenyl)-1-piperazinyl]propyl]-5-ethyl-2,4-dihydro-3H-1,2,4-triazol-3-one hydrochloride (5.4 g., 0.014 mole), pulverized potassium carbonate (5.8 g., 0.042 mole) and a trace of potassium iodide in 50 ml. of acetonitrile is refluxed for a 20 hr. period. The hot reaction mixture is filtered, the filtrate concentrated under reduced pressure and residual material taken up in chloroform and filtered. Solvent is removed and further purification carried out chromatographically employing a silica gel column with ethanol/chloroform eluent. The chromatographically purified material is taken up in ether and acidified with ethanolic hydrogen chloride to provide a solid which is triturated with ethanol to provide 1.6 g. (20% yield) of 4-[3-[4-(3-chlorophenyl)-1-piperazinyl]propyl]-5-ethyl-2,4-dihydro-2-(3-phenoxypropyl)-3H-1,2,4-triazol-3-one dihydrochloride hydrate, m.p. 146°–148° C.

Anal. Calcd. for $C_{26}H_{34}ClN_5O_2 \cdot 2HCl \cdot 0.75\ H_2O$: C, 54.75; H, 6.63; N, 12.28. Found: C, 55.03; H, 6.54; N, 12.49.

NMR (DMSO-$d_6$): 1.19 (3H, t, 7.3 Hz); 2.15 (4H, m); 2.62 (2H, q, 7.3 Hz); 3.20 (6H, m); 3.80 (8H, m); 4.01 (2H, t, 6.0 Hz); 6.96 (6H, m); 7.29 (3H, m); 7.78 (3H, bs); 11.80 (1H, bs).

EXAMPLE 4

4-[3-[4-(3-Chlorophenyl)-1-piperazinyl]propyl]-5-ethyl-2,4-dihydro-2-(4-phenoxybutyl)-3H-1,2,4-triazol-3-one (Ic)

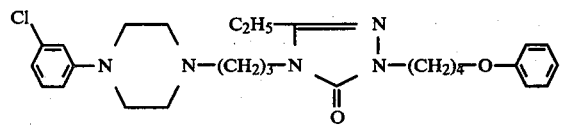

A mixture of 4-phenoxybutyl chloride (2.29 g., 0.01 mole), 4-[3-[4-(3-chlorphenyl)-1-piperazinyl]propyl]-5-ethyl-2,4-dihydro-3H-1,2,4-triazol-3-one hydrochloride (3.86 g., 0.01 mole), pulverized potassium carbonate (4.15 g., 0.03 mole) and a trace of potassium iodide in 50 ml. of acetonitrile is refluxed for a 65 hr. period. The hot reaction mixture is filtered, the filtrate concentrated under reduced pressure and residual material taken up in ether and filtered. Solvent is removed and further purification carried out chromatographically employing a silica gel column with ethanol/chloroform eluent. The chromatographically purified material is taken up in ethanol and acidified with ethanol hydrogen chloride to provide 2.17 g. of 4-[3-[4-(3-chlorophenyl)-1- piperazinyl]propyl]-5-ethyl-2,4-dihydro-2-(4-phenoxybutyl)-3H-1,2,4-triazol-3-one hydrochloride hyrate, m.p. 125°–127° C.

Anal. Calcd. for $C_{27}H_{36}ClN_5O_2 \cdot HCl \cdot \frac{1}{4} H_2O$: C, 60.17; H, 7.02; N, 13.00. Found: C, 60.19; H, 7.11; N, 12.89.

NMR (DMSO-$d_6$): 1.18 (3H, t; 7.4 Hz); 1.75 (4H, m); 2.16 (2H, m); 2.61 (2H, q, 7.4 Hz); 3.18 (6H, m); 3.80 (6H, m); 3.96 (4H, m); 6.92 (6H, m); 7.25 (3H, m); 11.75 (1H, bs).

EXAMPLE 5

Additional Formula I Products

By substituting the enumerated phenoxyalkyl halide for phenoxyethyl bromide in Example 2, alkylation of 4-[3-[4-(3-chlorophenyl)-1-piperazinyl]propyl]-5-ethyl-2,4-dihydro-3H-1,2,4-triazol-3-one is carried out to provide the indicated Formula I compounds.

|  | Compound | | |
|---|---|---|---|
|  | $R_1$ | n | Phenoxyalkyl halide |
| (Id) | 4-Cl | 2 | 4-chlorophenoxyethyl chloride |
| (Ie) | 3-Cl | 2 | 3-chlorophenoxyethyl chloride |
| (If) | 4-F | 2 | 4-fluorophenoxyethyl bromide |
| (Ig) | 4-F | 3 | 4-fluorophenoxypropyl chloride |
| (Ih) | 3-CH$_3$O | 2 | 3-methoxyphenoxyethyl chloride |
| (Ii) | 4-CH$_3$O | 2 | 4-methoxyphenoxyethyl chloride |

What is claimed is:

1. A compound of Formula I

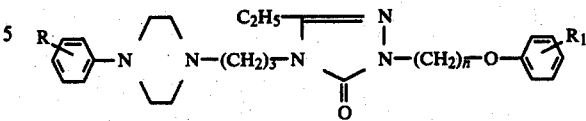

wherein $R_1$ is hydrogen, halogen or alkoxy of 1–4 carbon atoms, n is 2–4, R is halogen or a pharmaceutically acceptable acid addition salt thereof.

2. The compound of claim 1 which is 4-[3-[4-(3-chlorophenyl)-1-piperazinyl]propyl]-5-ethyl-2,4-dihydro-2-(2-phenoxyethyl)-3H-1,2,4-triazol-3-one.

3. The compound of claim 1 which is 4-[3-[4-(3-chlorophenyl)-1-piperazinyl]propyl]-5-ethyl-2,4-dihydro-2-(2-phenoxyethyl)-3H-1,2,4-triazol-3-one hydrochloride.

4. The compound of claim 1 which is 4-[3-[4-(3-chlorophenyl)-1-piperazinyl]propyl]-5-ethyl-2,4-dihydro-2-(3-phenoxypropyl)-3H-1,2,4-triazol-3-one.

5. The compound of claim 1 which is 4-[3-[4-(3-chlorophenyl)-1-piperazinyl]propyl]-5-ethyl-2,4-dihydro-2-(4-phenoxybutyl)-3H-1,2,4-triazol-3-one.

6. The method for treating a mammal afflicted with depression comprising administering to said mammal a therapeutically effective antidepressant amount of a compound of claim 1 or a pharmaceutically acceptable acid addition salt thereof.

7. The pharmaceutical composition comprising an antidepressant amount of a compound of claim 1 or a pharmaceutically acceptable acid addition salt thereof and a pharmaceutically acceptable carrier.

* * * * *